United States Patent [19]

Bradner

[11] 4,077,157

[45] Mar. 7, 1978

[54] HYBRIDIZATION OF SOYBEANS VIA THE LEAF-CUTTER BEE

[75] Inventor: Norman R. Bradner, Marshalltown, Iowa

[73] Assignee: Pfizer Inc., New York, N.Y.

[21] Appl. No.: 684,966

[22] Filed: May 10, 1976

[51] Int. Cl.$^2$ ............................................... A01H 1/02
[52] U.S. Cl. ..................................... 47/58; 47/DIG. 1
[58] Field of Search ........................... 47/58, 1, DIG. 1

[56] References Cited

U.S. PATENT DOCUMENTS 3,903,645   9/1975   Bradner ................................... 47/58

OTHER PUBLICATIONS

Pedersen et al. "Producing Seeds of Legumes" *Seeds the Yearbook of Agriculture* 1961.

McGregor, S. E. "InsectPollination-Significance and Research Needs" *American Bee Journal* vol. 113, Continued Article; Nos. 7, 8, & 9, pp. 249, 294, 295, 330 and 331, 7-9, 1973.

Stephen, W. P. et al. (1976) "X-Radiography, an Analytical Tool in Population Studies of the Leaf-Cutter Bees Megachile Pacifica" from the *Journal of Agricultural Research* vol. 52, No. 2, pp. 81-87.

Goplen, B. P. et al. (1975) "Alfalfa Flower Color Associated With Differential Seed Set by Leaf-Cutter Bees", *Agronomy Journal, vol. 67, pp. 804-806.*

Kehr, W. R. (1973) "Cross-Fertilization of Alfalfa as Affected by Genetic Markers Planting Methods, Locations, and Pollinator Species" *Crop Science* vol. 13, No. 3, pp. 296-298.

Bohart, G. E. (1970) "Commercial Production and Management of Wild Bees-a New Entomological Industry" *Bulletin of Entomological Society of America* vol. 16, No. 1, pp. 8-9.

Bohart, G. E. (1972) "Management of Wild Bees for the Pollination of Crops" *Ann. Rev. Entol.* vol. 17, pp. 287-312.

*Primary Examiner*—Edgar S. Burr
*Assistant Examiner*—James R. Feyrer
*Attorney, Agent, or Firm*—Connolly and Hutz

[57] ABSTRACT

A process for the efficient production of seed capable of growing $F_1$ hybrid soybean plants comprising the steps of:

(a) growing a first population of normal soybean plants characterized by relatively large seeds in pollinating proximity to a second population of soybean plants characterized by delayed pollen release and relatively smaller seeds, each of said populations being of the closed floret types;

(b) exposing the two plant populations to a population of leaf-cutter bees (*Megachile rotundata* L.);

(c) harvesting the seed crop which is formed on said plants of said second population; and (d) recovering from said harvested seed crop the relatively larger seed resulting from cross-pollination.

4 Claims, 1 Drawing Figure

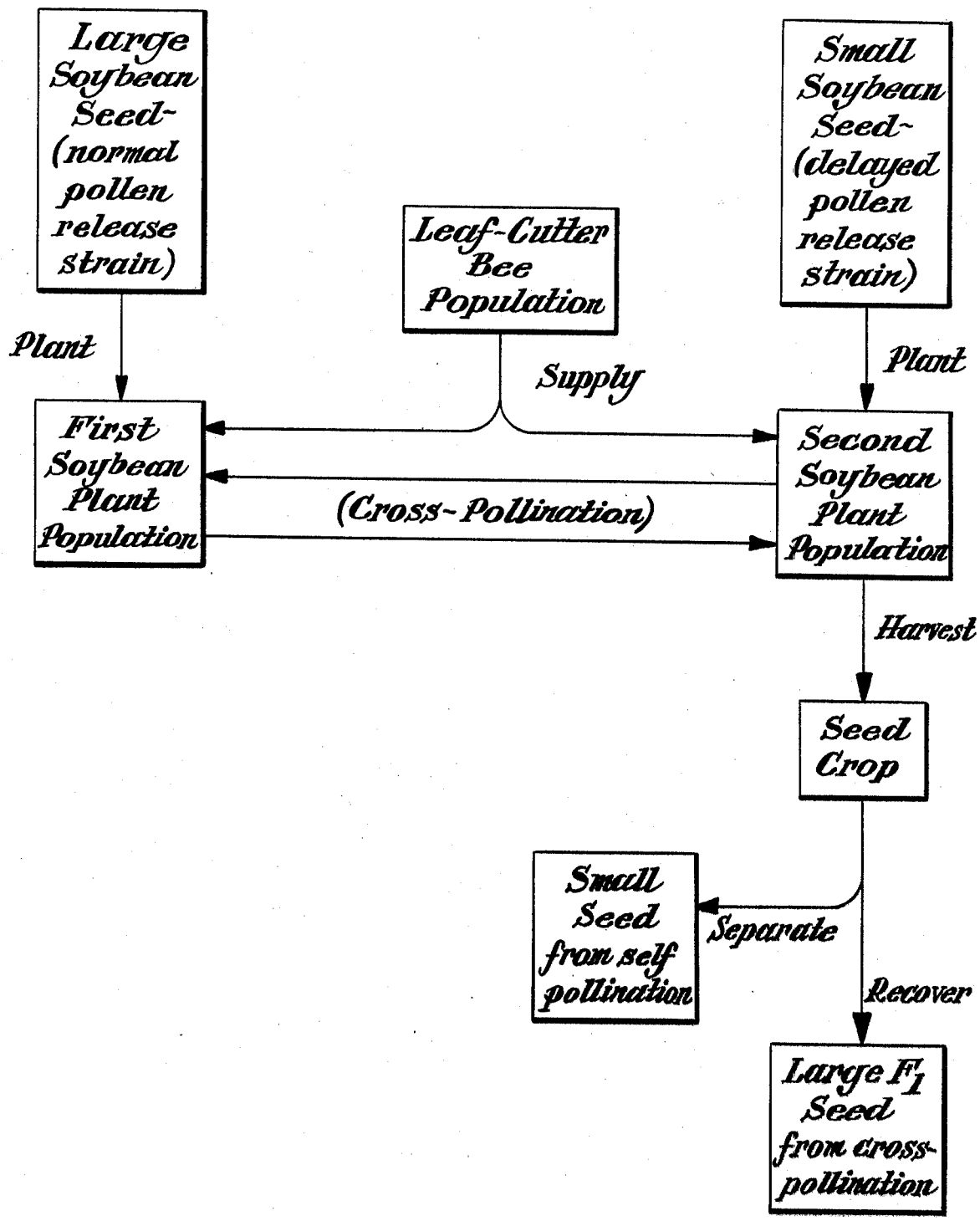

HYBRIDIZATION OF SOYBEANS VIA THE LEAF-CUTTER BEE

BACKGROUND OF THE INVENTION

It has been recognized for many years that the hybridization of closely related plants results in offspring having a combination of desirable traits which previously were possessed separately by the parent plants. Certain hybrid plants also have possessed a vigor or heterosis which has rendered them of considerable economic importance.

While significant advances have been made in the production of hybrid sugar beets, hybrid corn (see U.S. Pat. No. 2,753,663 to Jones), hybrid sorghum, and hybrid alfalfa (see U.S. Pat. No. 3,570,181 to Davis) many economically important crops remain in which no commercially practicable breeding technique has been developed for the production of a hybrid. Obviously cross-pollination carried out by hand is not feasible for commercial production. Much of the difficulty experienced when attempts have been made to develop a hybrid of many crops can be traced to the diverse reproduction systems and modes of pollination encountered. Accordingly, each crop must be approached separately and its unique characteristics taken into consideration.

Soybean plants (i.e. Glycine max plants) are recognized to be naturally self-pollinated plants which while being capable of undergoing cross-pollination rarely do so. Insects are reported by some researchers to carry pollen from one soybean plant to another but it generally is estimated that less than one percent of soybean seed formed in an open planting can be traced to cross-pollination, i.e., less than 1 percent of the soybean seed formed in an open planting is capable of producing $F_1$ hybrid soybean plants. See the articles by Elbert R. Jaycox entitled "Ecological Relationships between Honey Bees and Soybeans" appearing in the American Bee Journal, Vol. 110(8):306–307 (August 1970), Vol. 110(9):343–345 (September 1970) and Vol. 110(10):383–385 (October 1970).

The relatively low proportion of cross-pollination commonly observed in soybean plants when grown in nature can be traced to the characteristic floral configuration exhibited by soybean plants. The pistillate (female) and staminate (male) elements of soybean flowers are normally present on the same plant and are located within perfect flowers. The opening of the individual soybean flowers (florets) is believed to be triggered by the length of time the plant is exposed to light. However, the anthers and stigma continue to be tightly enclosed within petals (i.e. the portion of the flower known as the keel petals). When dehiscence of another tissue occurs and pollen is shed from the anthers, it tends immediately to contact the stigma in the same floret and is retained there by the keel petals. A seed pod ultimately is formed from this fertilization assuming that the pollen does not abort.

Some researchers have reported the existence of a degree of male sterility in selected soybean plants. See, for instance:

1. "A Partially Male Sterile Strain of Soybeans", by C. E. Caviness, H. J. Walters, and D. L. Johnson, Crop Science, Vol. 10, p 107–108, (Jan. - Feb. 1970), 2. "Inheritance of a Male-Sterile Character in Soybeans", C. A. Brim and M. F. Young, Crop Science, Vol. 11, p 564–566, (July - Aug. 1971), and 3. U.S. Pat. No. 3,903,645.

The last named reference disclosed the production of $F_1$ hybrid soybeans by growing a population of small seeded soybean plants of the open floret (exposed floral stigma) type in pollinating proximity to large seeded soybean plants having normal (closed) flowers. The reference further discloses that the open floret plants are preferably partially male sterile, i.e. characterized by delayed pollen release. It also discloses that process is conducted by random cross-pollination by pollen carrying insects, including honey bees, bumble bees, solitary bees, thrips and leaf-cutter bees.

Now it has been discovered that such $F_1$ hybrid soybeans can be produced on a commercial scale without recourse to the relatively rare open florate plants if leaf-cutter bees are provided for the cross-pollination and if the variety selected as the female parent exhibits delay pollen release.

DESCRIPTION OF THE DRAWING

The FIGURE illustrates in block diagram form the process of this invention whereby a leaf-cutter bee population is employed to cross-pollinate two different strains of soybean plants thereby producing a large $R_1$ hydrid soybean.

SUMMARY OF THE INVENTION

The present invention comprises a process for the efficient production of seed capable of growing $F_1$ hybrid soybean plants comprising the steps of:

(a) growing a first population of normal soybean plants in pollinating proximity to a second population of soybean plants characterized by delayed pollen release, each of said populations being of the closed floret type and said first population being characterized by relatively larger seeds than those of said second population upon self-pollination; (b) exposing the two plant populations to a population of leaf-cutter bees (Megachile rotundata L.); (c) havesting the seed crop which is formed on said plants of said second population; amd (d) recovering from said harvested seed crop the relatively larger seed resulting from cross-pollination.

A preferred process of the present invention is that in which said first and second populations are grown in alternating strips.

Another preferred process of the present invention is that in which at least a portion of said seed recovered in step d additionally is planted, the resulting $F_1$ hybrid plants are allowed to self-pollinate, and the thus formed $F_2$ seed is harvested.

Yet another preferred process of the present invention is that wherein the average seed weight of said first population exceeds the average seed weight of said second population by at least 6 grams per 100 seeds.

DETAILED DESCRIPTION OF THE INVENTION

The normal soybean plants employed as the first population in the present invention are preferably of a homogeneous stable soybean line and should be one which has a propensity to yield seed of a relatively large size upon self-pollination. The plants have the usual normal soybean floral configuration consisting of standard petals, wing petals, keel petals, sepals, and peduncle. The pistil and stamen are tightly enclosed within the keel petals even when the remainder of the floret is open. The keel petals never open up to expose the female flower parts to visit by insects or wind blown pollen (closed floret type). The normal plants preferably are good pollen producers and when serving as the pollen parent for seed produced upon the plants of the second population result in the production of an $F_1$ hybrid which exhibits a substantial degree of heterosis for seed yield. The normal soybean plants are also selected so that they bloom at approximately the same time as the soybean plants of the second population. Representative soybean plants from which the plants of the first population may be derived include the following large seeded varieties: Disoy, Sac, Portugal, Etum, Kanrich, and Plant Introduction (i.e. P.I.) Nos. 19.968, 70.243, 80.459, 85.441, 86.134–1, 89.162, 92.661, 196.160, and 290.149. Other large seeded varieties may be utilized as will be apparent to those skilled in the art.

Soybean plants of the second population are characterized by delayed pollen release and by the propensity to yield seed of a relatively small size with respect to the seed of the first population upon self-pollination. The plants are normal in other respects and have normal flowers (closed floret type) as described above.

Soybean plants suitable for use in the second population may be derived from plants located by examining soybean plants of existing varieties for the requisite characteristics. For example, soybean plants having the required delayed pollen release are found in populations of the Merit variety.

Soybean plants having the requisite delayed pollen release are tested for the reproducibility of this characteristic and developed into a homogeneous stable line or strain through conventional plant breeding techniques. Those plants having delayed pollen release may be developed into a homogeneous line having this, as well as the small seed size characteristic, by selection from the segregating population. The small seeded lines can be developed from existing small seeded varieties by standard backcrossing techniques. Plants having delayed pollen release can be selected in $F_2$ populations of the small seeded lines, and be maintained by normal selfing of the homozygous conditions. Representative small seeded varieties include: Merit, Norsoy, Seneca, Adams, and Plant Introduction (i.e. P.I.) Nos. 68.403, 70.077, 70.091, 70.241, 82.264, 85.505, 87.620, 96.162, 171.652, and 266.800A. Other small seeded varieties may be utilized as will be apparent to those skilled in the art.

Some variation in seed size may occur in a given soybean line or variety. This can be traced at least in part to environmental conditions and the presence or absence of abundant moisture at the time of seed set. However, a given soybean line tends to produce mature seed of a relatively constant or typical size assuming the environmental conditions are constant. When the populations are such that seed produced upon self-pollination of the plants of the first (normal) population is larger than that produced upon self-pollination of the plants of the second population, then the seed produced upon cross-pollination of the plants of the second population with pollen from the plants of the normal population is, in selected cases, larger than the seed formed thereon upon self-pollination. The seed formed upon cross-pollination tends, in selected cases, to be intermediate in size between that of the parents. Relative seed sizes for the two populations are selected so that an adequate size differential exists to facilitate expeditious physical segregation of the same (as described hereafter) depending upon whether cross-pollination or self-pollination produced the seed. For instance, the plants of the normal population preferably produce an average seed size upon self-pollination which exceeds that produced upon self-pollination of the plants of the second population by at least 6 grams per 100 seeds.

Prior to planting, the seed utilized to form the plants of the first and second populations may advantageously be inoculated with nitrogen fixing bacteria (i.e. Rhizobia) in accordance with conventional seed preparation techniques, particularly if planted where soybeans have not been grown previously.

In accordance with the process of the present invention the plants of the two populations are grown in pollinating proximity. The proximity of the two populations must be adequate to permit cross-pollination by the aid of pollen-carrying insects, particularly the leaf cutter bee. In a preferred embodiment of the process the soybean plants of the first and second populations are grown in alternating strips. The alternating strips may consist of one or more adjoining rows of the plants of each population. Usual soybean planting techniques (e.g. row widths of about 20 to 40 inches) may be utilized within a given population of the soybean plants.

The soybean plants of the two populations are randomly cross-pollinated with the aid of pollen-carrying insects and will also undergo a degree of self-pollination. As the insects forage for nectar and pollen, the pollen required for cross-pollination is transported. Representative pollen-carrying insects are honey bees, bumble bees, solitary bees, thrips, and in the case of plants with closed florets such as these soybean plants, especially the leaf-cutter bee, *Megachile rotundata L.*

In a preferred process of the present invention the soybean plants of the second population are also partially male sterile and produces less than the normal quantity of viable pollen commonly observed in soybean plants thereby tending to enhance the relative proportion of cross-pollination. Of course, the plants selected preferably exhibit a relatively high degree of female fertility. In theory, the partial male sterility utilized may be genetic or cytoplasmic in nature. Plants having this partial sterility are selected by examining soybean plants of existing varieties for pollen content and/or viability. Such partially sterile soybean strains are well known. When the sterility is genetically controlled the gene for partial male sterility is transferred into the soybean plants of the seed population in accordance with standard plant breeding techniques. When plants of the second population are partially male sterile it is preferred that the plants of the normal population contain a restorer factor or gene so that all of the $F_1$ hybrid plants produced are completely male fertile (i.e. the plants of the normal population are homozygous dominant for fertility restoration). In a particularly preferred embodiment of the process the soybean plants of the second population exhibit both the delayed dehiscence characteristic and the partial male sterility characteristic.

In a further preferred process of the present invention the soybean plants of the second population additionally include a genetic marker which visually can be observed in progeny plants when cross-pollination occurs within the plants of the second population and which is absent in the progeny plants when cross-pollination occurs. The genetic marker can take the form of a recessive gene which no longer manifests itself when a dominant gene for the characteristic in question is derived upon cross-pollination. The plants of the first and second populations should be homozygous for the presence and absence of the characteristic in question. The genetic marker may be selected from any one of a variety of recessive characteristics and preferably is readily observable in the progeny should self-pollination occur. For instance, the genetic marker can be a distinctive pubescence color (e.g. gray pubescence vs. tawny pubescence), flower color (e.g. white flowers vs. purple flowers), seed coat color (e.g. yellow vs. black seed coat color), distinctive seed appearance (e.g. plain yellow vs. mottled yellow appearance), and hilum appearance, (e.g. yellow vs. black hilum), etc. The preferred genetic markers are pubescence color and flower color. The use of a genetic marker enables one readily to determine the $F_1$ purity of the seed harvested from the plants of the second population following physical separation of the same on the basis of size (described hereafter). For instance, a sample of the relatively larger seed resulting from the separation may be grown, and the purity of the larger seed with respect to $F_1$ hybrid content determined by observing the incidence of the dominant genetic marker in the resulting plants. Alternatively, the incidence of the recessive genetic marker can be observed as an indication of the proportion of seed resulting from self-pollination. If desired, the observation for the marker may be done mechanically, e.g. by use of a photoelectric cell.

The soybean lines of the first and second populations preferably are also bred to exhibit adequate resistance to disease, insects, and lodging.

Following seed set and seed maturation the seed which has formed upon the plants of the second population is selectively harvested to the substantial exclusion of seed which has formed upon the plants of the normal population. The seed which has formed upon the plants of the normal population may also be selectively recovered and utilized primarily for non-planting purposes. Harvesting and seed removal from the pods is carried out in the usual manner. Selective harvesting can be carried out with ease when the plants of the normal and second populations are separated by a blank row. The seed produced upon the plants of the second population will be in two generally different sizes with the smaller seed resulting from self-pollination and the larger seed resulting from cross-pollination.

The seed from the plants of the second population is physically segregated wherein the relatively larger seed resulting from cross-pollination which is capable of growing $F_1$ hybrid soybean plants is separated from the relatively smaller seed resulting from self-pollination. The physical separation conveniently may be made in any of the equipment commonly utilized for the cleaning and size grading of seeds. Representative devices include screens, indent and cylinder separators, gravity tables, etc. If the genetic marker system previously discussed should indicate that the $F_1$ hybrid seed resulting from the separation is not sufficiently pure, an additional, more refined seed size separation may be carried out. For instance, during the winter a sample of the seed may be grown out in a greenhouse and the incidence of the marker determined.

In a representative separation the seed for planting the second population will pass a 14/64 inch screen and collect on a 12/64 inch screen, the seed for planting the first population will pass a 24/64 inch screen and collect on a 20/64 inch screen, and the seed capable of growing $F_1$ hybrid soybean plants will pass a 24/64 inch screen and collect on a 16/64 inch screen. Any seed from the female parent which passes the 16/64 inch screen is assumed to be the result of self-pollination. These seed sizes are not to be construed as limiting, since they may be varied depending on the particular soybean plants available to serve as parent populations. They merely serve to illustrate the way in which parent plants producing on self-pollination relatively large and relatively small seed with respect to each other facilitate the recovery of the hybrid seed which results on cross-pollination in the process of the invention.

The relatively larger seed resulting from cross-pollination may be planted directly to yield soybeans in enhanced yields, or advantageously used as foundation seed for the production of planting seed (i.e. $F_2$ seed) which continues to exhibit an appreciable degree of enhanced vigor (i.e. heterosis with respect to seed yield) following the self-pollination of the same. Normally approximately one-half of seed production heterosis exhibited in the $F_1$ hybrid is present in the $F_2$ generation following self-pollination. In this manner the seed readily may be multiplied to produce a commercially superior planting seed.

The present process is believed to offer a superior commerically practicable route to the production of seed capable of growing $F_1$ hybrid soybean plants.

The ability of the farmer to plant either the $F_1$ hybrid soybean seed, or the $F_2$ seed resulting from the self-pollination of the $F_1$ seed offers significant advantages. An increased yield over existing varieties (typically about 15 to 25 percent) can be expected when the $F_1$ hybrid soybean seed is planted, and an increased yield over existing varieties (typically about 7 to 12 percent) can be expected when the $F_2$ seed is planted.

Although the invention has been described with peferred embodiments, it is to be understood that variations and modifications may be resorted to as will be apparent to those skilled in the art. Such variations and modifications are to be considered within the purview and scope of the claims appended hereto. For example, the process of the present invention wherein the plants of the second population additionally produce less than the normal quantity of viable pollen grains is also desirable.

The example to follow is merely illustrative and in no way limits the scope of the claims.

EXAMPLE

Type A and Type B soybean plants were grown in alternating rows separated by about 30 inches. The type A plants were the normal closed floret fertile Corsoy variety of purple flower line which ordinarily produce relatively large seed (about 16.5 grams per 100 seeds) which passes a 12/64 inch screen and collects on an 11/64 inch screen. The Type B plants were closed floret soybean plants of white flower line, characterized by delayed pollen release which ordinarily produce relatively small seed (about 10.5 grams per 100 seeds) passing an 11/64 inch screen and collecting on a 10/64 inch screen.

The plants were grown in 12' by 12' cages and when mature flowers appeared, leaf-cutter bees (*Megachile rotundata* L. female) were released, 20 bees per cage. Following seed set and maturation, the seed crop was collected from the plants of Type B only, and sifted to retrieve seed which passed a 10.5/64 inch screen and collected on a 10/64 inch screen, rejecting seed which passed the 10/64 inch screen.

When planted and grown, a sample of this seed produced $F_1$ soybean plants which exhibited 86 purple flowers and 163 white flowers, demonstrating 34.5% cross-pollination to the desired hybrid. The $F_2$ seed crop resulting from self-pollination of these plants can be planted to produce another generation of hybrid soybean plants.

In a control experiment, the foregoing procedure was repeated, this time employing, in place of the Type B plants, Type C closed floret soybean plants of white flower line characterized by normal pollen release (fertile) which ordinarily produce seed passing an 11/64 inch screen and collecting on a 10/64 inch screen. When planted and grown, a sample of the Type C seed crop produced soybean plants which exhibited 1 purple flower and 65 white flowers, demonstrating only 1.5% cross-pollination to the desired hybrid.

What is claimed is:

1. A process for the efficient production of seed capable of growing $F_1$ hybrid soybean plants comprising the steps of:
    (a) growing a first population of normal soybean plants in pollinating proximity to a second population of soybean plants characterized by delayed pollen release, each of said populations being of the closed floret type and said first population being characterized by relatively larger seeds than those of said second population upon self-pollination;
    (b) exposing the two plant populations to a population of leaf-cutter bees (*Megachile rotundata L.*) sufficiently large to cause extensive cross-pollination;
    (c) harvesting the seed crop which is formed on said plants of said second population; and (d) recovering from said harvested seed crop the relatively larger seed resulting from cross-pollination.

2. A process according to claim 1 wherein said first and second populations are grown in alternating strips.

3. A process according to claim 1 wherein at least a portion of said seed recovered in step *d* is planted, the resulting $F_1$ hybrid plants are allowed to self-pollinate, and the thus formed $F_2$ seed is harvested.

4. A process according to claim 1 wherein the average seed weight of said first population exceeds the average seed weight of said second population by at least 6 grams per 100 seeds.

* * * * *